(12) United States Patent
Finke et al.

(10) Patent No.: US 9,750,484 B2
(45) Date of Patent: Sep. 5, 2017

(54) METHOD AND DEVICE TO EXAMINE A TISSUE SAMPLE

(71) Applicant: Siemens Aktiengesellschaft, Munich (DE)

(72) Inventors: Ilka Finke, Erlangen (DE); Daniel Fischer, Heroldsberg (DE)

(73) Assignee: Siemens Aktiengesellschaft, Munich (DE)

( * ) Notice: Subject to any disclaimer, the term of this patent is extended or adjusted under 35 U.S.C. 154(b) by 318 days.

(21) Appl. No.: 14/480,872

(22) Filed: Sep. 9, 2014

(65) Prior Publication Data

US 2015/0073298 A1 Mar. 12, 2015

(30) Foreign Application Priority Data

Sep. 9, 2013 (DE) ......... 10 2013 217 961

(51) Int. Cl.
*A61B 5/05* (2006.01)
*A61B 10/02* (2006.01)
*A61B 5/06* (2006.01)
*A61B 6/00* (2006.01)
*A61B 6/02* (2006.01)

(52) U.S. Cl.
CPC .............. *A61B 10/02* (2013.01); *A61B 5/061* (2013.01); *A61B 6/025* (2013.01); *A61B 6/502* (2013.01)

(58) Field of Classification Search
CPC ......... A61B 10/02; A61B 6/025; A61B 5/061; A61B 6/502
USPC ................................. 600/407–430
See application file for complete search history.

(56) References Cited

U.S. PATENT DOCUMENTS

| 4,821,727 | A | 4/1989 | Levene et al. | |
|---|---|---|---|---|
| 5,078,142 | A | 1/1992 | Siczek et al. | |
| 7,826,588 | B2 * | 11/2010 | Eliasson | A61B 6/502 378/37 |
| 9,439,616 | B2 * | 9/2016 | Mahameed | A61B 6/5205 |
| 2004/0114714 | A1 * | 6/2004 | Minyard | A61B 5/0002 378/37 |
| 2009/0003519 | A1 * | 1/2009 | Defreitas | A61B 6/502 378/37 |
| 2009/0171244 | A1 * | 7/2009 | Ning | A61B 6/032 600/567 |
| 2010/0016713 | A1 | 1/2010 | Welch | |

(Continued)

FOREIGN PATENT DOCUMENTS

CN 102327122 A 1/2012

*Primary Examiner* — Sanjay Cattungal
(74) *Attorney, Agent, or Firm* — Schiff Hardin LLP

(57) ABSTRACT

In a method and an apparatus to exam a tissue sample, a female breast is compressed in an x-ray imaging apparatus and a biopsy procedure is conducted to extract a tissue sample from the compressed breast, with the extraction taking place using images generated by the x-ray imaging system. While the breast is still compressed, the extracted tissue sample is transported to a region outside of the extraction location that is irradiated by x-rays from the x-ray source of the imaging apparatus, and is irradiated at that region by the x-ray source in order to generate 3D data from a radiation detector that are used to reconstruct a data set of slice images from common projections of the extraction region and the tissue sample. The reconstructed slice images are then displayed.

16 Claims, 1 Drawing Sheet

(56) References Cited

U.S. PATENT DOCUMENTS

| | | | |
|---|---|---|---|
| 2010/0054402 A1* | 3/2010 | Fischer | A61B 6/08 378/37 |
| 2010/0249648 A1 | 9/2010 | Nakata | |
| 2012/0022358 A1* | 1/2012 | Fischer | A61B 6/025 600/407 |
| 2012/0022401 A1* | 1/2012 | Fischer | A61B 10/0233 600/567 |
| 2012/0053455 A1 | 3/2012 | Okada | |
| 2013/0158388 A1* | 6/2013 | Blevis | A61B 10/0233 600/424 |

* cited by examiner

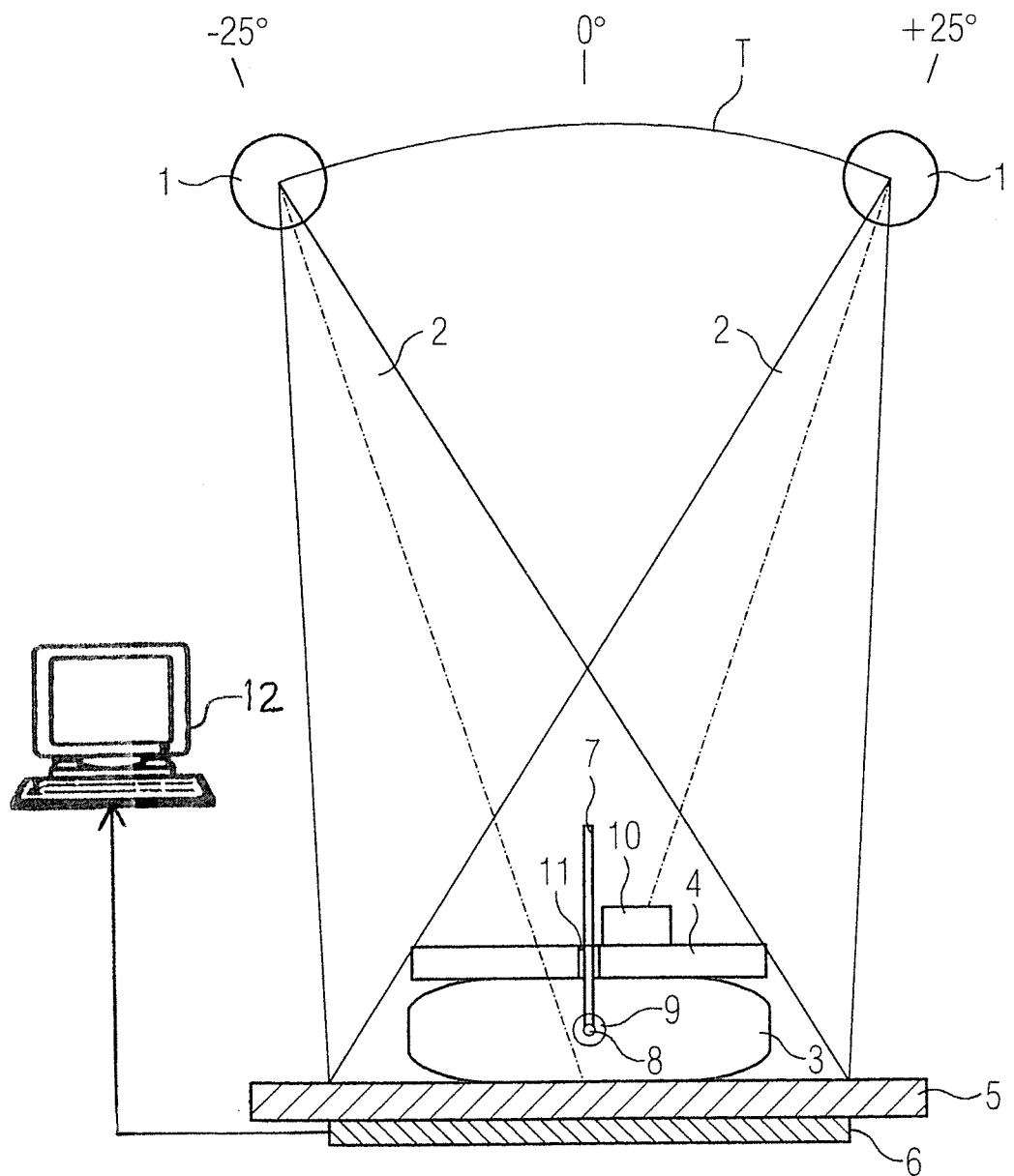

METHOD AND DEVICE TO EXAMINE A TISSUE SAMPLE

BACKGROUND OF THE INVENTION

Field of the Invention

The invention concerns a method to examine a tissue sample and a device to examine a tissue sample.

Description of the Prior Art

Examination of a tissue sample can be implemented after an extraction of the tissue sample from a living organism (biopsy).

In such a biopsy, for example, the tissue sample is extracted from the breast and is histologically examined. The extraction most often takes place with the aid of an imaging method. Stereotactic biopsy is an established examination method. For this purpose, the breast to be examined is compressed in a mammography apparatus between a support plate and a compression plate that can be displaced with respect to the support plate. A first x-ray image acquisition (scout image, 0° acquisition, overview acquisition) subsequently takes place with an x-ray source. Using this x-ray image acquisition a check is made as to whether the region to be examined is correctly positioned. For this purpose, an x-ray detector is typically integrated into the support plate.

The subsequent acquisitions typically take place in pairs from two different directions (what are known as stereo acquisitions). Given a stationary support plate, the x-ray source is moved in an angle range of +/−25° on a circular arc around the vertical axis. In the first two stereo acquisitions, the target (for example tumor or microcalcification) is marked, and from this the precise penetration position and penetration depth for the biopsy needle can be determined. The biopsy needle is subsequently introduced into the breast and the position of the biopsy needle is monitored by additional stereo acquisitions. In the case of a vacuum biopsy, the biopsy needle tip is located just before reaching the lesion and the needle is introduced into the relevant tissue with a firing mechanism that is a component of the biopsy unit. The tissue sample is removed by a lateral opening in the biopsy needle and—in the case of a vacuum biopsy—is transported into a sample container outside of the breast. In the case of microcalcifications, the sample is examined with the aid of an x-ray device in order to check the result of the biopsy. This can take place either at an extra x-ray system or at the biopsy system. However, for this purpose the breast must be uncompressed. An additional extraction of a sample under identical conditions with regard to the compression of the breast is thus not possible.

Examinations known as tomosynthesis examinations are often implemented with a mammography apparatus. For this purpose, a sequence of tomosynthesis projections is created, for example 25 projections, wherein the x-ray source (x-ray radiator) rotates over the detector in an angle range between −25° and +25°. The x-ray radiation is thus triggered at regular intervals of 2°, and a respective projection is read out from the x-ray detector. The three-dimensional subject is subsequently reconstructed from the projections in a tomosynthesis reconstruction process. The evaluation of the reconstruction result takes place in z-slices, i.e. in slices that are parallel to the x-ray detector.

SUMMARY OF THE INVENTION

An object of the present invention is to provide a method with which a quick examination of an extracted tissue sample can be implemented. Furthermore, it is an object of the present invention to provide a device with which a quick examination of an extracted tissue sample can be implemented.

According to the invention, a method for the examination of a tissue sample includes the following features.

A tissue sample is extracted at an extraction location in a biopsy.

The tissue sample is transported into a position outside of the extraction location.

The tissue sample is placed in a region outside of the extraction location, this region being with a region irradiated by x-ray radiation from an x-ray source.

An x-ray-based 3D monitoring acquisition is implemented using the x-ray source.

A data set of slice images is reconstructed from common projections of the extraction location and the tissue sample.

The reconstructed slice images are displayed.

A device according to the invention includes the following features.

An x-ray device has an x-ray source and an x-ray detector.

A support plate for an examination subject and a compression plate for compression of the examination subject are provided.

A biopsy unit that has a biopsy needle to extract a tissue sample at an extraction location, and a deposition device transports the tissue sample extracted from the examination subject.

The deposition device is situated outside of the extraction location and in a region exposed by the x-ray source.

An evaluation unit reconstructs a data set of slice images from common projections of the extraction location and the tissue sample, as well as to present the reconstructed slice images.

In the method according to the invention, the extracted tissue sample is initially transported into a position outside of the extraction location in order to be subsequently placed in a region outside of the extraction location. This region is irradiated by the x-ray radiation.

Because the region is located outside of the extraction location (and therefore outside of the compressed examination subject), but lies within the region irradiated by the x-ray radiation, the examination subject does not need to be uncompressed. A quick examination of the extracted tissue sample therefore can be implemented with the method according to the invention.

In the device according to the invention, the deposition device for the tissue sample extracted from the examination subject is situated outside of the extraction location, but in a region exposed by the x-ray source. With the use of the device according to the invention, the examination subject thus does not need to be uncompressed, such that a quick examination of the extracted tissue sample can be implemented with the device according to the invention.

Given the method and the device according to the invention, a new compression of the examination subject does not need to be made because the tissue sample is placed in a region outside of the extraction location, and this region is irradiated by the x-ray radiation. This ensures that additional extractions of tissue samples can be made under identical conditions. In addition to a shorter examination time, a greater certainty is ensured given a new extraction of tissue samples. Since the position of the examination subject does not need to be modified during the examination, additional x-ray devices are not required.

The method and device according to the invention thus make it possible to implement a quick examination of a tissue sample.

In an embodiment of the method, the tissue sample is transported into a position above the extraction location. In an associated embodiment of the device, the deposition device is arranged above the extraction location. In a further embodiment of the method and the device according to the invention, a manual positioning of the tissue sample is not needed. According to a preferred embodiment, the deposition device for the tissue sample is fashioned as a sample container.

In a further embodiment, the implementation of the x-ray-based 3D monitoring exposure is advantageously implemented in a partial angle range.

According to a further preferred embodiment, the x-ray-based 3D monitoring acquisition is a tomosynthesis acquisition.

According to another embodiment, the slice images of the tomosynthesis acquisition are presented as a maximum intensity projection.

In a further embodiment, the reconstruction of a data set for the extraction location and the reconstruction of a data set for the tissue sample are respectively implemented.

In a further embodiment a synthetic mammogram is generated from the slice images of the tissue sample.

In another preferred embodiment, the compression plate has a feedthrough for the biopsy needle. In such a device, in addition to a horizontal extraction of a tissue sample, a vertical extraction of a tissue sample is also possible.

According to another embodiment of the device, the x-ray detector is integrated into the support plate.

BRIEF DESCRIPTION OF THE DRAWING

The single FIGURE schematically illustrates an embodiment of a device according to the invention, in a sectional view.

DESCRIPTION OF the PREFERRED EMBODIMENTS

The embodiment of the device for examination of a tissue sample, as presented in the single FIGURE, is designed as a mammography apparatus.

The mammography apparatus has an x-ray source 1 that emits x-ray radiation 2 that irradiates (exposes) an examination subject 3. The examination subject 3 is a female breast that is fixed between a compression plate 4 and a support plate 5. The x-ray radiation 2 passing through the examination subject 3, the compression plate 4 and the support plate 5 is detected by a large-area x-ray detector 6. The x-ray detector 6 is, for example, a large-area digital x-ray detector that is composed of a number of individual detectors arranged in a matrix-like array.

The device shown in the drawing furthermore has a biopsy unit. The biopsy unit has a biopsy needle 7 to extract a tissue sample 8 from an extraction location 9 in the examination subject 3, as well as a deposition device 10.

In the presented exemplary embodiment, the deposition device 10 is executed as a sample container and arranged above the extraction location 9 and above the compression plate 4. The tissue sample 8 is thus placed outside of the extraction location 9 after being deposited in the sample container 10.

Although the sample container 10 is arranged outside of the extraction location 9, the sample container 10 (deposition device) is, in a region acquired by the x-ray radiation 2.

The compression plate 4 has a feedthrough 11 for the biopsy needle 7. In addition to a horizontal extraction of a tissue sample 8 (for which no feedthrough 11 in the compression plate 4 is required), a vertical extraction of a tissue sample 8 is therefore also possible. In the shown exemplary embodiment, a vertical extraction of the tissue sample 8 is depicted.

Before an extraction of a tissue sample 8 from the examination subject 3 is begun, an overview acquisition at the position 0° must be made with the x-ray source 1. With this x-ray image acquisition a check is made as to whether the region to be examined is positioned correctly.

A 3D data acquisition (monitoring acquisition) is subsequently implemented to monitor the tissue within the examination subject 3 (in particular in the extraction location 9) as well as in the adjacent regions, which may thus include all or some of the still-compressed breast (subject 3). In order to acquire data for this purpose, 2D projections are obtained by moving the x-ray source 1 on a trajectory T in an angle range from −25° to +25°, with 2D irradiations (projections) occurring respectively at successive incremental angle positions in this range.

Furthermore, the mammography apparatus shown in the single FIGURE has an evaluation unit 12. The evaluation unit 12 serves to reconstruct a data set of slice images from common projections of the extraction location 9 and of the tissue sample 8, as well as to present the reconstructed slice images at a display screen.

In the method according and the device according to the invention, a new compression of the examination subject 3 (breast) does not need to be made because the tissue sample 8 is placed in a region outside of the extraction location 9, and this region is irradiated by the x-ray radiation 2. It is therefore ensured that additional extractions of tissue samples 8 are made under identical conditions. In addition to a shorter examination time, a greater certainty is also ensured in the new extraction of tissue samples 8. Since the position of the examination subject 3 does not need to change during an examination, additional x-ray sources and/or additional x-ray detectors are not required.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to examine a tissue sample, comprising:
   compressing an examination subject between a compression plate and a radiation detector in an x-ray imaging apparatus comprising an x-ray source that emits x-ray radiation in a field of view of said x-ray source;
   conducting a biopsy of the compressed examination subject to extract a tissue sample from an extraction location within the examination subject, using x-ray images generated with said x-ray imaging system;
   while the examination subject is still compressed, transporting the extracted tissue sample to a region that is within said field of view of said x-ray source but that is outside of said extraction location;
   while said examination subject is still compressed, acquiring a 3D data set that includes both said extraction region, and said extracted tissue sample at said region outside of said extraction location, by moving said x-ray source through a plurality of positions and irradiating said extracted tissue sample and said extraction region from each of those positions in order to generate a plurality of common projections of both the extraction region and the extracted tissue sample;

while the examination subject is still compressed, reconstructing slice images that show both of the extracted tissue sample and the extraction region from said common projections; and while the examination subject is still compressed, displaying the reconstructed slice images at a display screen.

2. A method as claimed in claim 1 comprising transporting the extracted tissue sample to a region above the extraction location.

3. A method as claimed in claim 1 comprising acquiring said 3D data by moving said x-ray source through an angle range that is less than 360°.

4. A method as claimed in claim 1 comprising acquiring said 3D data set as a tomosynthesis data set.

5. A method as claimed in claim 1 comprising implementing a separate reconstruction of a data set representing said extraction region and a reconstruction of a data set representing said tissue sample.

6. A method as claimed in claim 1 wherein said examination subject is a female breast, and generating a synthetic mammogram from said slice images of said tissue sample wherein said tissue sample is depicted in an image of said female breast.

7. A method as claimed in claim 1 comprising generating said slice images of said examination subject as a tomosynthesis exposure of said examination subject and presenting said slice images at said display screen as a maximum intensity projection.

8. An apparatus to examine a tissue sample, comprising:
an x-ray imaging apparatus comprising an x-ray source that emits x-ray radiation, a radiation detector, and a compression plate that compresses an examination subject between the compression plate and the radiation detector;
a biopsy apparatus configured to conduct a biopsy of the compressed examination subject to extract a tissue sample from an extraction location within the examination subject, using x-ray images generated with said x-ray imaging system;
a sample container into which the tissue sample is transported from said extraction while the examination subject is still compressed, said x-ray imaging apparatus comprising a location at which said sample container is situated that is outside of said extraction location but within said field of view of said x-ray source;
said x-ray imaging apparatus being configured to acquire a 3D data set that includes both said extraction region and said extracted tissue sample in said sample container at said location outside of said extraction location while said examination subject is still compressed, by moving said x-ray source through a plurality of positions and irradiating said tissue sample and said region from each of those positions to generate a plurality of common projections of both the extraction region and the extracted tissue sample;
a computer configured to reconstruct slice images of the tissue sample and the extraction region from said common projections while said examination subject is still compressed; and
said computer being configured to display the reconstructed slice images at a display screen while said examination subject is still compressed.

9. An apparatus as claimed in claim 8 wherein said location is in a region above the extraction location.

10. An apparatus as claimed in claim 8 wherein said x-ray imaging apparatus is configured to acquire said 3D data by moving said x-ray source through an angle range that is less than 360°.

11. An apparatus as claimed in claim 8 wherein said x-ray imaging apparatus is configured to acquire said 3D data set as a tomosynthesis data set.

12. An apparatus as claimed in claim 8 wherein said computer is configured to implement separate reconstruction of a data set representing said extraction region and a reconstruction of a data set representing said tissue sample in said sample container.

13. An apparatus as claimed in claim 8 wherein said examination subject is a female breast, and wherein said computer is configured to generate a synthetic mammogram from said slice images of said tissue sample wherein said tissue sample is depicted in an image of said female breast.

14. An apparatus as claimed in claim 8 wherein said computer is configured to generate said slice images of said examination subject as a tomosynthesis exposure of said examination subject and to present said slice images at said display screen as a maximum intensity projection.

15. An apparatus as claimed in claim 8 wherein said biopsy apparatus is configured to implement said biopsy using a biopsy needle, and wherein said compression plate comprises a feedthrough opening therein through which said biopsy needle is inserted into said examination subject.

16. An apparatus as claimed in claim 8 wherein said x-ray imaging apparatus comprises a support plate into which said radiation detector is integrated, with said examination subject being compressed between said compression plate and said support plate.

* * * * *